US00PP26263P2

(12) United States Plant Patent
Hartman

(10) Patent No.: US PP26,263 P2
(45) Date of Patent: Dec. 22, 2015

(54) ***CALADIUM* PLANT NAMED 'SANGRIA'**

(50) Latin Name: *Caladium×hortulanum*
Varietal Denomination: Sangria

(71) Applicant: Robert Dale Hartman, Lake Placid, FL (US)

(72) Inventor: Robert Dale Hartman, Lake Placid, FL (US)

( * ) Notice: Subject to any disclaimer, the term of this patent is extended or adjusted under 35 U.S.C. 154(b) by 201 days.

(21) Appl. No.: 13/998,475

(22) Filed: Nov. 4, 2013

(51) Int. Cl.
*A01H 5/12* (2006.01)

(52) U.S. Cl.
USPC ..... Plt./373

(58) Field of Classification Search
USPC ..... Plt./373
See application file for complete search history.

*Primary Examiner* — Anne Grunberg
(74) *Attorney, Agent, or Firm* — C. A. Whealy

(57) ABSTRACT

A new and distinct cultivar of *Caladium* plant named 'Sangria', characterized by its short to intermediate in height, upright and uniformly mounded plant habit; vigorous growth habit and rapid growth rate; undulate lance-type leaves that have rose red-colored centers and contrasting dark green-colored margins; and good landscape performance.

4 Drawing Sheets

Botanical designation: *Caladium×hortulanum.*
Cultivar denomination: 'SANGRIA'.

BACKGROUND OF THE INVENTION

The present invention relates to a new and distinct cultivar of *Caladium* plant, botanically known as *Caladium×hortulanum*, commercially referred to as a lance (strap) leaf-type *Caladium* and hereinafter referred to by the name 'Sangria'.

The objective of the Inventor's breeding program is to create new *Caladium* plants that have uniform plant habit, exceptional container and garden performance and attractive and unique leaf coloration.

The new *Caladium* plant originated from a cross-pollination made by the Inventor in April, 2008 in Avon Park, Fla. of *Caladium×hortulanum* 'John Peed', not patented, as the female, or seed, parent with *Caladium×hortulanum* 'White Wonder', disclosed in U.S. Plant Pat. No. 21,044, as the male, or pollen, parent. The new *Caladium* plant was discovered and selected by the Inventor as a single plant within the progeny of the stated cross-pollination in a controlled outdoor nursery environment in Zolfo Springs, Fla. on September, 2009.

Asexual reproduction of the new *Caladium* plant by 'chipping' the tubers (cutting the tuber into segments with each segment containing an axillary bud and tuber cortical tissue) in a controlled outdoor nursery environment in Lake Placid, Fla. since April, 2010 has shown that the unique features of this new *Caladium* plant are stable and reproduced true to type in successive generations of asexual reproduction.

SUMMARY OF THE INVENTION

Plants of the new *Caladium* have not been observed under all possible environmental conditions and cultural practices. The phenotype may vary somewhat with variations in environmental conditions such as temperature and light intensity, without, however, any variance in genotype.

The following traits have been repeatedly observed and are determined to be the unique characteristics of 'Sangria'.

These characteristics in combination distinguish 'Sangria' as a new and distinct *Caladium* plant:

1. Short to intermediate in height, upright and uniformly mounded plant habit.
2. Vigorous growth habit and rapid growth rate.
3. Undulate lance-type leaves that have rose red-colored centers and contrasting dark green-colored margins.
4. Good landscape performance and relatively tolerant to high light conditions.

Plants of the new *Caladium* differ primarily from plants of the female parent, 'John Peed', in the following characteristics:

1. Plants of the new *Caladium* are slightly shorter than plants of 'John Peed'.
2. Plants of the new *Caladium* are faster growing and produce finished plants about one week earlier than plants of 'John Peed'.
3. Plants of the new *Caladium* and 'John Peed' differ in leaf shape and color as leaves of plants of 'John Peed' are fancy-types with dark red-colored centers and dark green-colored margins.
4. Plants of the *Caladium* and 'John Peed' differ in leaf petiole coloration.

Plants of the new *Caladium* differ primarily from plants of the male parent, 'White Wonder', in the following characteristics:

1. Plants of the new *Caladium* are slightly taller than plants of 'White Wonder'.
2. Plants of the new *Caladium* are slower growing and produce finished plants about one week later than plants of 'White Wonder'.
3. Plants of the new *Caladium* and 'White Wonder' differ in leaf color as leaves of plants of 'White Wonder' are white to grey-green in color with red-colored basal notches, light pink to white-colored venation and dark green-colored borders.
4. Plants of the *Caladium* and 'White Wonder' differ in leaf petiole coloration.

Plants of the new *Caladium* can be compared to plants of *Caladium×hortulanum* 'Florida Sweetheart', disclosed in U.S. Plant Pat. No. 8,526. In side-by-side comparisons, plants of the new *Caladium* differed primarily from plants of 'Florida Sweetheart' in the following characteristics:

1. Plants of the new *Caladium* were slightly taller than plants of 'Florida Sweetheart'.
2. Plants of the new *Caladium* were faster-growing and produced finished plants about one week earlier than plants of 'Florida Sweetheart'.
3. Plants of the new *Caladium* and 'Florida Sweetheart' differed in leaf color as leaves of plants of 'Florida Sweetheart' were pink in color with greenish white-colored margins and rose pink-colored venation.
4. Plants of the new *Caladium* and 'Florida Sweetheart' differed in leaf petiole color.

Plants of the new *Caladium* can be compared to plants of *Caladium×hortulanum* 'Rosemary', disclosed in U.S. Plant Pat. No. 20,993. In side-by-side comparisons, plants of the new *Caladium* differed primarily from plants of 'Rosemary' in the following characteristics:

1. Plants of the new *Caladium* were shorter than plants of 'Rosemary'.
2. Plants of the new *Caladium* produced finished plants about one week later than plants of 'Rosemary'.
3. Plants of the new *Caladium* and 'Rosemary' differed in leaf color as leaves of plants of 'Rosemary' had rose red-colored centers with mottled light and dark green-colored borders.
4. Plants of the new *Caladium* and 'Rosemary' differed in leaf petiole color.

BRIEF DESCRIPTION OF THE PHOTOGRAPHS

The accompanying photographs illustrate the overall appearance of the new *Caladium* plant showing the colors as true as it is reasonably possible to obtain in colored reproductions of this type. Colors in the photographs may differ slightly from the color values cited in the detailed botanical description which accurately describe the colors of the new *Caladium* plant.

The photograph on the first sheet is a side perspective view of a typical plant of 'Sangria' in a 15-cm container and grown in a shadehouse.

The photograph at the top of the second sheet is a side perspective view of typical plants of 'Sangria' grown in an open field.

The photograph at the bottom of the second sheet is a close-up view of typical freshly-harvested tubers and roots of 'Sangria' plants.

The photograph on the third sheet is close-up view of developing and fully developed inflorescences of 'Sangria'.

The photograph at the top of the fourth sheet is a comparison view of typical potted plants of the female parent, 'John Peed' (left), 'Sangria' (center) and the male parent, 'White Wonder' (right).

The photograph at the bottom of the fourth sheet is a comparison view of typical potted plants of 'Florida Sweetheart' (left), 'Sangria' (center) and 'Rosemary' (right).

DETAILED BOTANICAL DESCRIPTION

The aforementioned photographs and following observations and measurements describe plants grown in 15-cm containers in a polypropylene-covered shadehouse (30% light reduction) in Avon Park, Fla. and plants grown in ground beds under full sunlight in an outdoor nursery in Crewsville, Fla. The plants were grown under cultural practices typical of commercial shadehouse and outdoor nursery production. During the production of the plants, day temperatures ranged from about 29° C. to 35° C. (shadehouse) or 28° C. to 33° C. (outdoor nursery), night temperatures ranged from about 23° C. to 26° C. (shadehouse) or 22° C. to 25° C. (outdoor nursery) and light levels were about 8,000 foot-candles (shadehouse) or 10,000 to 12,000 foot-candles (outdoor nursery). Plants grown in the shadehouse were seven weeks old and plants grown in the outdoor nursery were eight months old when the photographs and the detailed description were taken. In the following description, color references are made to The Royal Horticultural Society Colour Chart, 2001 Edition, except where general terms of ordinary dictionary significance are used.

Botanical classification: *Caladium×hortulanum* 'Sangria'.

Parentage:

*Female, or seed, parent.*—*Caladium×hortulanum* 'John Peed', not patented.

*Male, or pollen, parent.*—*Caladium×hortulanum* 'White Wonder', disclosed in U.S. Plant Pat. No. 21,044.

Propagation:

*Type.*—By "chipping" the tubers.

*Time to initiate roots, summer.*—About seven to ten days at 32° C.

*Time to initiate roots, winter.*—About two to three weeks at 24° C.

*Tuber description* (*outdoor nursery-grown plants*).—Appearance: Multi-segmented and somewhat flattened; individual segments elliptic to ovate in shape. Height: About 2.4 cm. Diameter: About 3.7 cm. Segment height: About 2.3 cm. Segment diameter: About 2.3 cm. Texture: Thick, starchy; somewhat brittle. Color: Epidermis, freshly-harvested: Close to 199D tinged with close to N199D. Epidermis, dried: Close to 200A to 200B. Cortical tissue: Close to 3D. Axillary buds: Close to 36A to 36B. Root description: Thick, fleshy contractile roots; color, close to 155C, proximally, faintly tinged with close to 182B to 182C. Rooting habit: Medium density.

Plant description:

*Plant type.*—Herbaceous perennial; suitable as a potted plant in containers 15-cm to 25-cm and suitable as a landscape plant in shaded areas.

*Plant and growth habit.*—Short to intermediate in height, upright and uniformly mounded plant habit; vigorous and dense growth habit; rapid growth rate, potted plants in finished or saleable form in about seven to eight weeks after planting tubers; leaf petioles and leaves arise from one or more growing points on tubers; petioles mostly upright and leaning outwardly with development.

*Plant height, from soil level to top of foliar plane, shadehouse-grown potted plants.*—About 19 cm to 22 cm.

*Plant height, from soil level to top of inflorescences, shadehouse-grown potted plants.*—About 30 cm.

*Plant diameter or spread, shadehouse-grown potted plants.*—About 48 cm to 50 cm.

*Number of shoots per plant, shadehouse-grown potted plants.*—About three to four shoots develop per #1 tuber.

*Cataphylls, shadehouse-grown potted plants.*—Length: About 7 cm to 10 cm. Width: About 1.2 cm to 1.8 cm. Shape: Wedge-shaped. Apex: Acute. Base: Sheathing the stem. Color, inner surface: Close to between N155C and N170D. Color, outer surface: Close to N170D tinged with close to 38D and streaked and stippled with close to N199A; with development, color becoming closer to 199B stained with close to 187C.

Leaf description:

*Arrangement and type*.—Alternate; simple; lance-type.

*Length, shadehouse-grown potted plants*.—About 16 cm to 22 cm.

*Width, shadehouse-grown potted plants, flattened*.—About 13 cm to 17 cm.

*Shape*.—Ovate, tending towards deltoid.

*Apex*.—Acuminate to acute.

*Base*.—Sagittate to sagittate-peltate.

*Margin*.—Entire; wavy with broad undulations.

*Texture, upper surface*.—Smooth, glabrous; somewhat rigid; dull sheen.

*Texture, lower surface*.—Smooth, glabrous; glaucous.

*Venation pattern*.—Pinnate.

*Color, shadehouse-grown potted plants*.—Developing and fully expanded leaves, upper surface: Main colors: Center, close to 53B tinged with close to 59C; towards the margins, close to 185A; margins, close to 147A and N189A; narrow leaf edge, close to 187B. Basal notch: Close to 53B tinged with closer to 59C. Midrib and primary venation: Close to between 53A and 187C. Developing and fully expanded leaves, lower surface: Main colors: Center, close to between 59A and 187B; towards the margins, close to 191A; narrow leaf edge, close to 187B. Basal notch: Close to between 59A and 187B. Midrib and primary venation: Close to 183A to 183B and 187B.

*Petiole*.—Aspect: Initially upright and straight; with development, leaning outwardly and curving; flexible. Length, shadehouse-grown potted plants: About 18 cm to 21 cm. Diameter, distal, shadehouse-grown potted plants: About 3.5 mm to 4 mm. Diameter, proximal, shadehouse-grown potted plants: About 6 mm to 10 mm. Color, shadehouse-grown potted plants, Just below the leaf and petiole junction: Close to 181A streaked with close to 184B; occasionally, variably striped with close to 200A. Overall: Close to 182C to 182D tessellated, streaked and stippled with close to 200C tinged with close to 147A to 147B; occasionally, variably striped with close to 200A. Wing length, shadehouse-grown potted plants: About 5 cm to 7 cm. Wing diameter, shadehouse-grown potted plants: About 5 mm to 12 mm. Wing color, shadehouse-grown potted plants, inner surface: Close to between N170D and N155C. Wing color, shadehouse-grown potted plants, outer surface: Close to 181D variably streaked and stippled with close to 200C to 200D tinged with close to 147B.

Inflorescence description: Inflorescences observed on eight week-old shadehouse-grown potted plants.

*Inflorescence arrangement*.—Upright hooded spathes surrounding a columnar spadix borne on a tall upright scape; spadix with sessile, simple female and male flowers separated into two zones; female flowers develop on the lower one-third of the spadix; male flowers develop on the upper two-thirds of the spadix; sterile flowers develop at junction of female and male flower zones; near this junction, the spathe constricts and surrounds and encloses the female flowers; spathe open and cupped around male flowers.

*Fragrance*.—Night-fragrant; sweet, jasmine-like with camphor note.

*Natural flowering season and flower longevity*.—Plants of the new *Caladium* typically flower during the spring in central Florida; flowers develop about eight weeks after growth commences; inflorescences last about three days before fading; inflorescences persistent.

*Spathe*.—Length, overall: About 9.3 cm. Length, distal open portion: About 6.5 cm. Length, proximal closed portion: About 2.8 cm. Width, distal open portion: About 3.2 cm. Width, at constriction: About 1.7 cm. Width, proximal closed portion: About 2.9 cm. Shape: Obovate to elliptic. Apex: Acuminate. Base: Obtuse. Margin: Entire. Texture, front and rear surfaces: Smooth, glabrous. Color, front surface: Distal open portion: Close to 159C; towards the margins, faintly tinged with close to 185D; with development, color becoming closer to 199D and N170D. Proximal closed portion: Close to 138C; distally, darkly flushed with close to N186C; color does not change with development. Color, rear surface: Distal open portion: Close to between 160D and 159D; towards the margins, faintly tinged with close to 185D; color does not change with development. Proximal closed portion: Close to 147B to 147C and 138B flushed with close to 184B and 185D; color does not change with development.

*Spadix*.—Length: About 7.9 cm. Length, male flower zone: About 5 cm. Length, sterile zone: About 1.3 cm. Length, female flower zone: About 1.6 cm. Diameter, male flower zone: About 9 mm. Diameter, sterile flower zone: About 7 mm. Diameter, female flower zone: About 8 mm. Shape: Columnar. Apex: Obtuse to bluntly acute. Base: Obtuse. Aspect: Upright. Color, mature, male zone: Close to 158B and 18D. Color, mature, sterile zone: Close to 158B. Color, mature, female zone: Close to 20D and 37D. Male flowers: Quantity per spadix: About 120. Shape: Obovate. Height: About 3 mm. Diameter: About 3.5 mm. Pollen amount: Abundant. Pollen color: Close to 6D. Female flowers: Quantity per spadix: About 109. Shape: Obovate. Height: About 2.5 mm. Diameter: About 1.5 mm. Stigma color: Close to 20D. Ovary color: Close to 37D.

*Scape*.—Length: About 20.7 cm. Diameter: About 5 mm. Strength: Sturdy; flexible. Aspect: Mostly erect. Texture: Smooth, glabrous; glaucous. Color, just below spathe: Close to 177D and 182D tinged and streaked with close to 184B. Color, overall: Close to 177D and 182D, streaked, stippled and tessellated with close to 200C.

*Seeds and fruits*.—Seed and fruit development have not been observed on plants of the new *Caladium*.

Disease & pest tolerance: Plants of the new *Caladium* have been observed to have above average tolerance to *Xanthomonas* Leaf Spot and to have average tolerance to *Pythium* Root Rot. Plants of the new *Caladium* have not been observed to have resistance to pests and other pathogens common to *Caladium* plants.

Temperature tolerance: Plants of the new *Caladium* have been observed to be tolerant to temperatures ranging from about 7° C. to about 40° C. and are suitable for USDA Hardiness Zones 8A to 11.

It is claimed:

1. A new and distinct *Caladium* plant named 'Sangria' as illustrated and described.

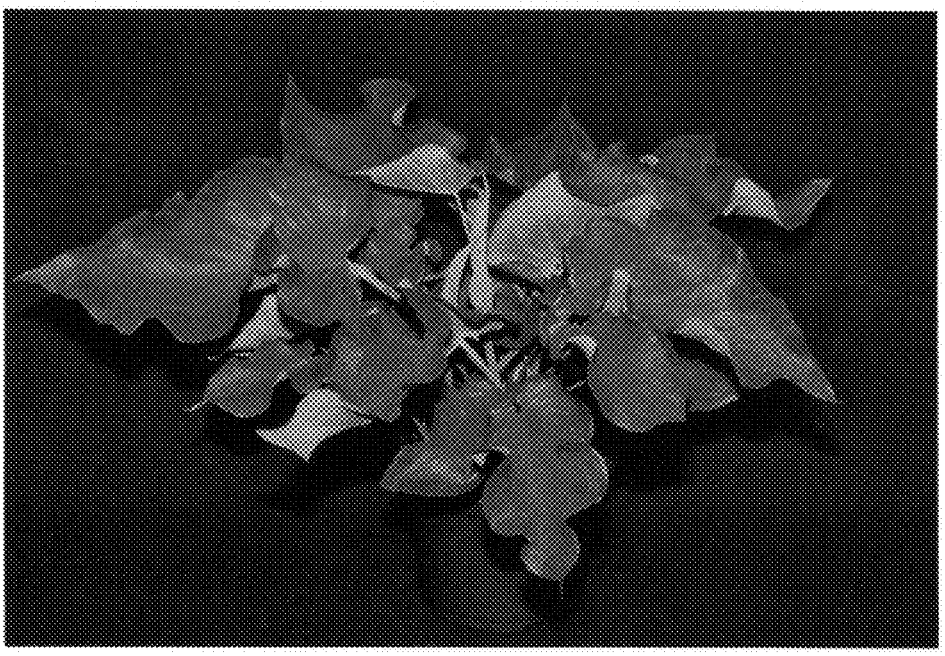

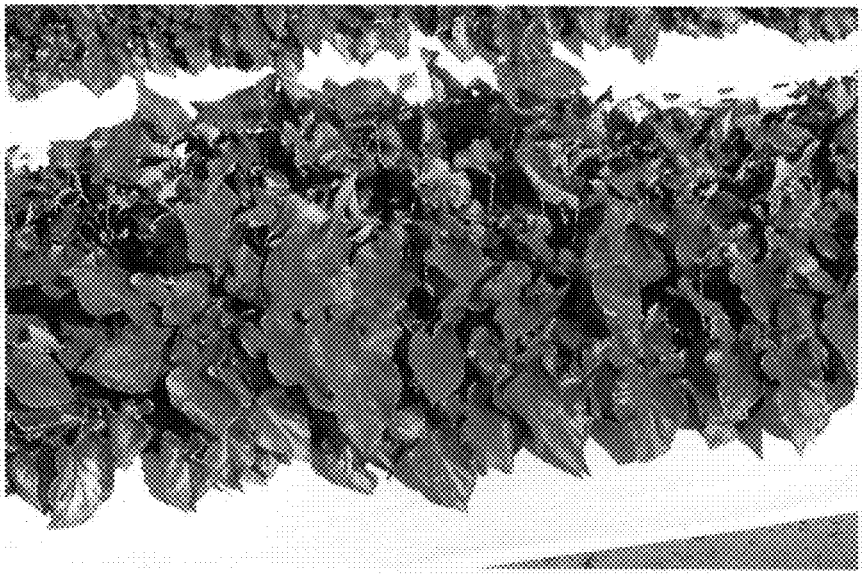
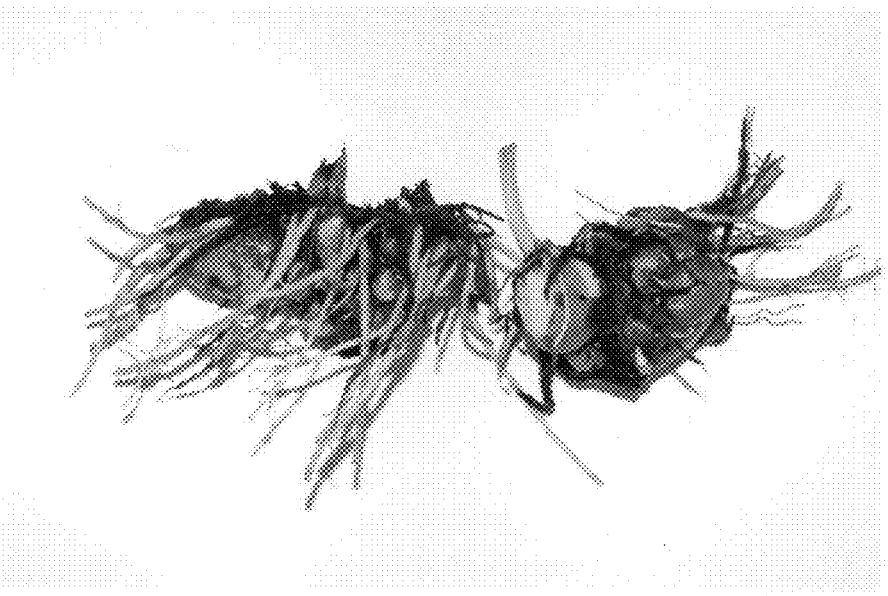

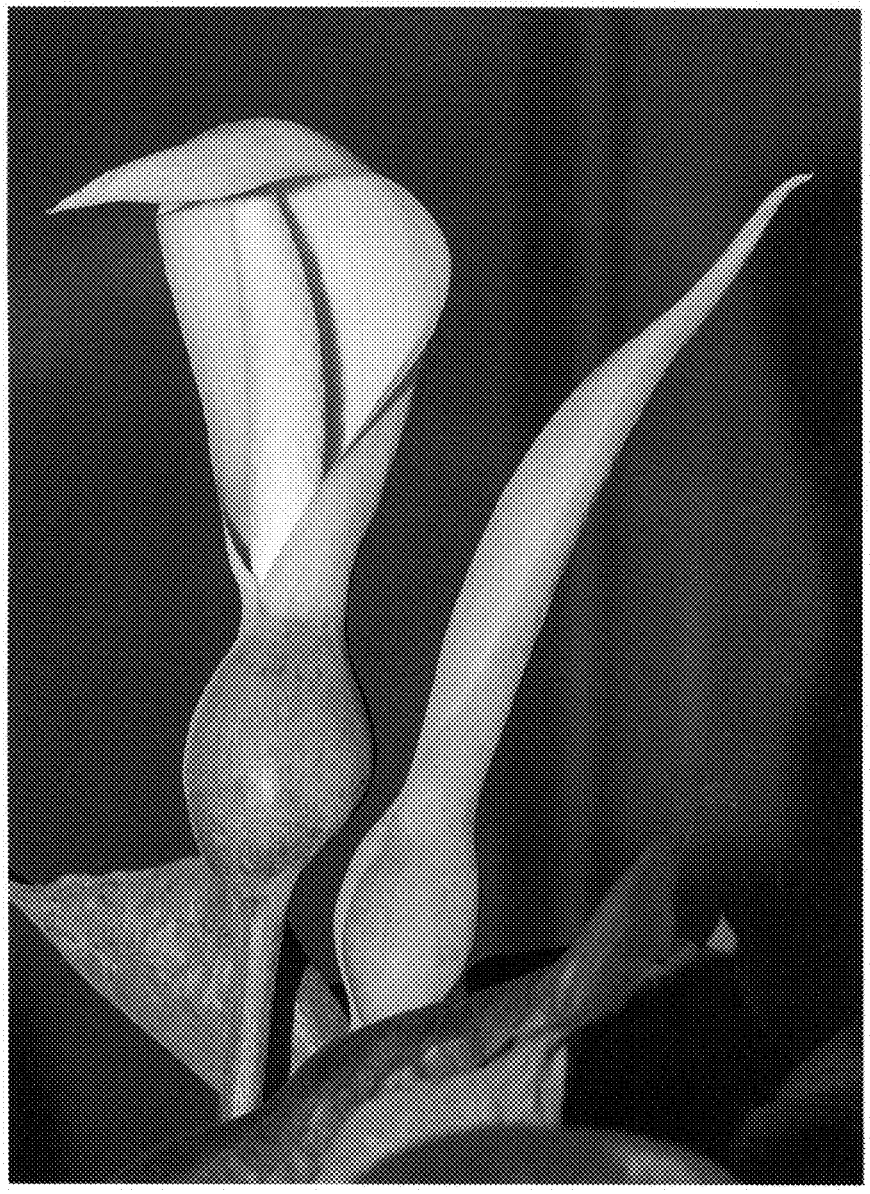

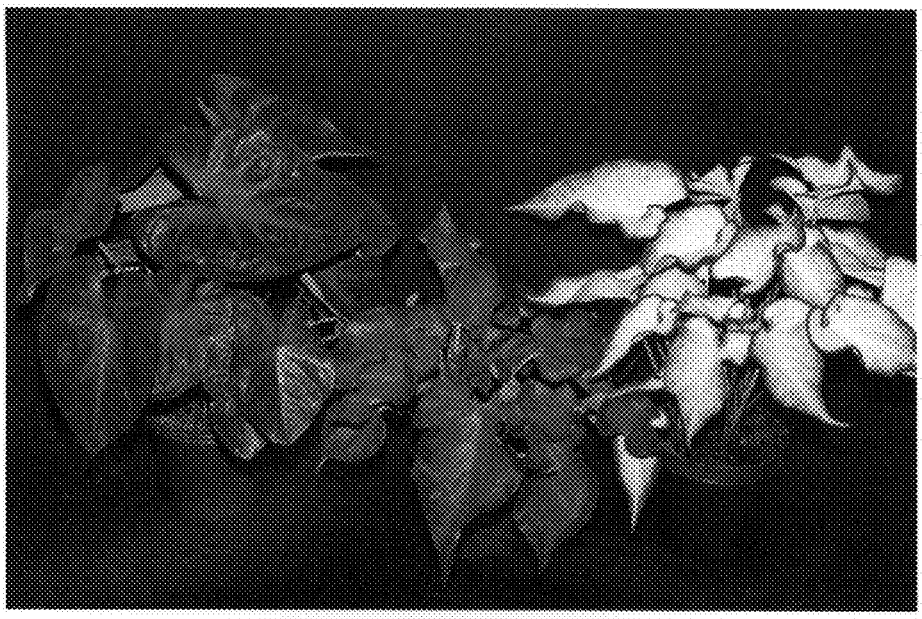
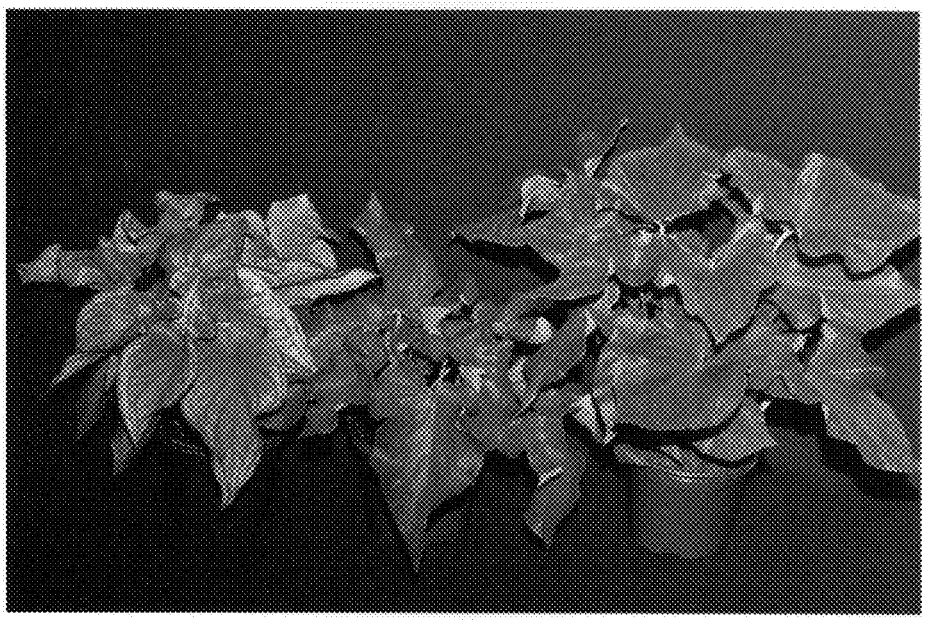

* * * * *